United States Patent [19]

Paris et al.

[11] Patent Number: 5,126,440
[45] Date of Patent: Jun. 30, 1992

[54] IODINATED POLYMERS WITH DEXTRAN SKELETON, PROCESSES FOR THEIR PREPARATION AND THEIR USES AS CONTRAST PRODUCTS

[75] Inventors: Dominique Paris, L'Abergement Clemencia; Michel Schaefer, Chilly-Mazarin; Didier Doucet, Livry-Gargan; Dominique Meyer, Saint Maur, all of France

[73] Assignee: Guerbert S.A., Villepinte, France

[21] Appl. No.: 474,735

[22] PCT Filed: Aug. 10, 1989

[86] PCT No.: PCT/FR89/00409
§ 371 Date: Apr. 10, 1990
§ 102(e) Date: Apr. 10, 1990

[87] PCT Pub. No.: WO90/01500
PCT Pub. Date: Feb. 22, 1990

[30] Foreign Application Priority Data
Aug. 10, 1988 [FR] France .................. 88 10794

[51] Int. Cl.⁵ .............. A61K 29/02; A61K 49/04; C08B 37/02; C08G 73/00
[52] U.S. Cl. ..................... 536/112; 424/5; 424/4; 514/59
[58] Field of Search ......... 536/112; 424/4, 5; 430/80; 514/59

[56] References Cited

U.S. PATENT DOCUMENTS

| | | | |
|---|---|---|---|
| 2,708,174 | 5/1955 | Stavely | 514/59 |
| 4,069,306 | 1/1978 | Rothman | 536/112 |
| 4,406,878 | 9/1983 | DeBoer | 424/5 |
| 4,822,594 | 4/1989 | Gibby | 536/112 |

FOREIGN PATENT DOCUMENTS

| | | | |
|---|---|---|---|
| 0146455 | 6/1985 | European Pat. Off. | 536/112 |
| 2610935 | 8/1988 | France | 536/112 |
| 1400985 | 7/1975 | United Kingdom | 536/112 |

Primary Examiner—Ronald W. Griffin
Assistant Examiner—Louise Leary
Attorney, Agent, or Firm—Young & Thompson

[57] ABSTRACT

The invention relates to iodine-containing polymers including a skeleton comprised of a dextrane to which are grafted groups having the formula (I), wherein the groups R are simultaneously groups derived from triiodobenzenic amines and groups derived from aliphatic amines.

4 Claims, No Drawings

IODINATED POLYMERS WITH DEXTRAN SKELETON, PROCESSES FOR THEIR PREPARATION AND THEIR USES AS CONTRAST PRODUCTS

The present invention relates to iodinated polymers which can be used in radiography as contrast products and, in particular, as injectable contrast products.

The compounds used as injectable contrast products must not only absorb X-rays but also possess various properties and in particular
adequate water solubility at physiological pHs,
a low toxicity,
an appropriate osmolarity
a chemical stability in the organism and to sterilization.

Up to now it has been necessary to inject considerable amounts of contrast products into patients in order to obtain a correct diagnosis starting from the radiographic image. Also, the researches have been oriented towards derivatives with a more suitable osmolarity and reduced toxicity Two new categories of products have thus made their appearance: ionic products of low osmolarity and non-ionic products More recently, one has tried to develop another approach consisting of slowing down the diffusion of the contrast products in the extra-vascular space.

For this purpose, different iodinated polymers have been suggested It is thus that U.S. Pat. No. 3,852,341 describes iodinated polymers obtained by copolymerization of a 3,5-diacylamino-2,4,6-triiodobenzene acid with bifunctional compounds such as a diepoxide. These polymers are soluble in water. FR-A-2,200,018 describes related copolymers which are cross-linked and insoluble in water.

U.S. Pat. No. 4,406,878 describes an iodinated polymer which is obtained by reaction of tetraiodphthalic anhydride on polyvinyl alcohol and cross-linking.

The applicant has already developed iodinated polymers which comprise a skeleton constituted by a dextran on which are grafted groups displaying a triiodobenzene residue.

These polymers are obtained in particular by conversion of the hydroxy groups of the dextran into grafting groups of the carboxymethyloxy type and reaction of the grafting groups of the carboxymethyloxy type thus obtained with amines containing a triiodobenzene residue.

The applicant has observed that the grafting of the amines onto the grafting groups of the carboxymethyloxy type is not complete and that 20 to 70% of the grafting groups of the carboxymethyloxy type do not react.

The applicant has now discovered that by making an aliphatic amine react on the grafting groups of the carboxymethyloxy type or analogous grafting groups which remain after reaction with an amine with a triiodobenzene residue, it was possible to obtain an iodinated polymer which exhibits a better tolerance.

Consequently, the object of the present invention is iodinated polymers comprising a skeleton constituted by a dextran on which are grafted groups of general formula:

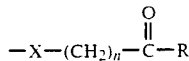

in which
X is selected from among the groups

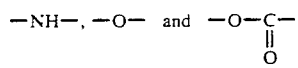

n is equal to 0 to 4 and the R groups are simultaneously
a) iodinated groups of formula

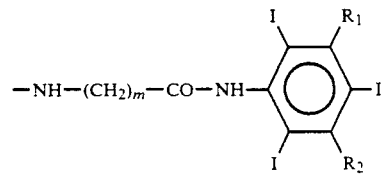

in which m is an integer from 1 to 5
$R_1$ is a group selected from among the COOH group, the COOH group made into a salt by a pharmaceutically acceptable base and the groups of formula

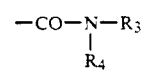

and
$R_2$ is a group selected from among the groups of formula

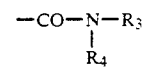

and

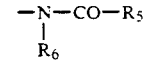

formulae in which
$R_3$ and $R_5$ are selected from among $C_1$ to $C_6$ alkyl, $C_1$ to $C_6$ hydroxyalkyl, $C_1$ to $C_6$ polyhydroxyalkyl, $(C_1-C_6)$ alkoxy $(C_1-C_6)$ alkyl and $(C_1-C_6)$ alkoxy $(C_1-C_6)$ hydroxyalkyl groups,
$R_4$ and $R_6$ are selected from among a hydrogen atom and $C_1$ to $C_6$ alkyl, $C_1$ to $C_6$ hydroxyalkyl, $C_1$ to $C_6$ polyhydroxyalkyl, $(C_1-C_6)$ alkoxy $(C_1-C_6)$ alkyl and $(C_1-C_6)$ alkoxy $(C_1-C_6)$ hydroxylakyl groups,
$R_3$ being, in addition, a group of formula

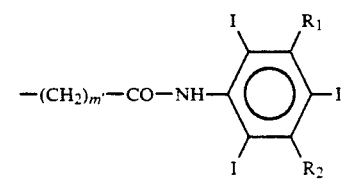

$m'$ being an integer from 1 to 5 and
$R_1$ and $R_2$ having the meaning given previously, b) non-iodinated groups of formula

—NH—R'

R' being a group selected from among $C_1$-$C_4$ alkyl, $C_1$-$C_4$ hydroxyalkyl and ($C_1$-$C_4$) polyhydroxyalkyl groups. and c) less than 20% of hydroxy groups.

The dextran which serves as support for the triiodobenzene groups is a polymer usually obtained from sucrose by the action of Leuconostoc mesenteroides.

The dextrans are polymers constitute by α-D-glucose units. The glycosyl units of chains are linked essentially by 1→6 linkages according to the following scheme

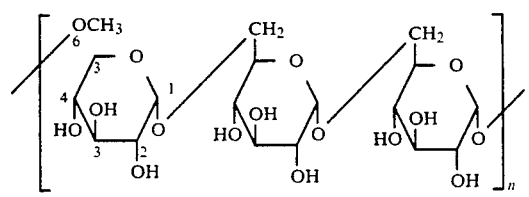

The commercial dextrans are usually subjected to a partial hydrolysis followed by fractionation in order to obtain more homogeneous polymers from the point of view of the molecular mass.

The dextrans used in the present invention may, in particular, have masses from 3,000 to 150,000 and preferably have masses from 10,000 to 100,000 in order to provide sufficiently watersoluble iodinated polymers.

The polymers according to the invention can be obtained by a process in which a) a grafting reagent is made to react on a dextran so as to convert the hydroxy groups of the dextran into grafting groups of formula $$-X-(CH_2)_n-\overset{O}{\overset{\|}{C}}-Z \quad (IV)$$

in which X and n have the meaning given previously and Z represents an activation group.

b) on the dextran presenting grafting groups thus obtained is made to react an amine of formula

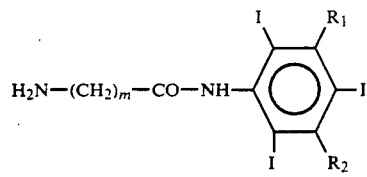

in which m, $R_1$ and $R_2$ have the meaning given previously and c) on the iodinated polymer thus obtained ismade to react an amine of formula $H_2N-R'$ (VI)

R' having the meaning given previously.

The method with monochloroacetic acid can be used in particular for the attachment of grafting groups.

This method consists of making the monochloroacetic acid react in alkaline medium according to the following reaction scheme

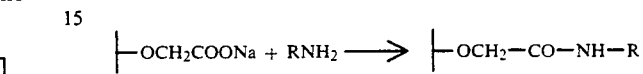

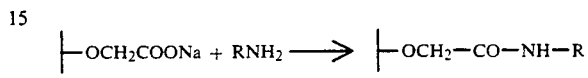

In a general manner, the reaction of the carboxymethyl dextran obtained with an amine $RNH_2$ leads to a dextran on which are grafted —$OCH_2$—CO—NHR groups according to the following scheme ⊢—$OCH_2COONa$ + $RNH_2$ ⟶ ⊢—$OCH_2$—CO—NH—R According to the present, an amine with a triiodobenzene group of formula V then an aliphatic amine of formula VI are used successively as amines.

In practice, the reactions with the amines require a coupling agent. For this purpose coupling agents classically used for the synthesis of peptides such as the carbodiimides and N-ethoxy carbonyl-2-ethoxy-1,2-dihydroquinoline(EEDQ) can be used. Hexamethyldisilazane of formula $(CH_3)_3SiNHSi(CH_3)_3$ can also be used as coupling agent.

The method with succinic anhydride can also be used for the attachment of the grafting groups.

This method consists of making succinic anhydride react in a polar solvent on the dextran by utilizing 4-dimethylaminopyridine as acylation catalyst, according to the following reaction scheme

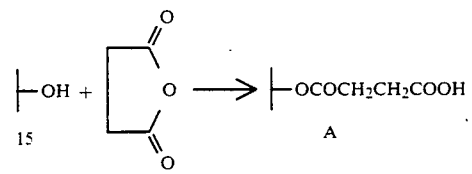

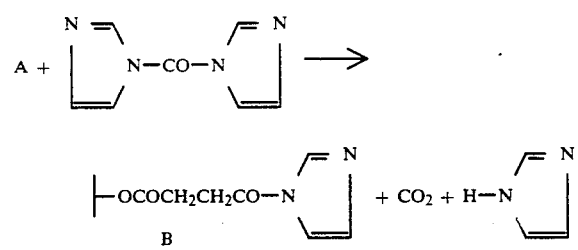

The activated polymer B can then react with amines $RNH_2$ according to the following reaction scheme

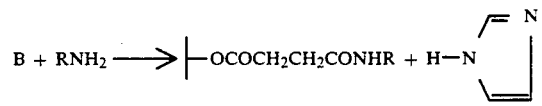

Iodinated amines of formula V are described in particular in FR-A-2272640. As examples of such amines may be mentioned the amines of the following formulae

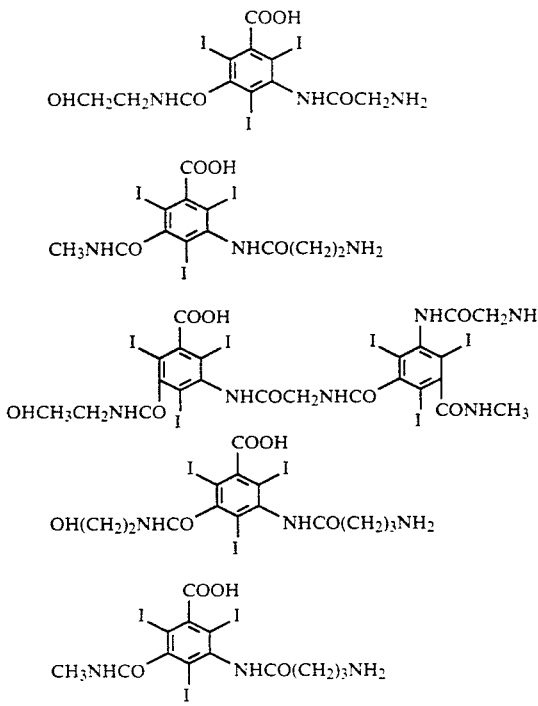

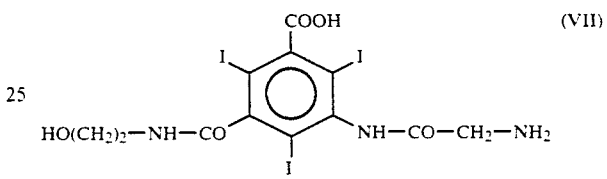

The following examples 1 to 9 illustrate the first two stages of the preparation of the iodinated polymers. Example 10 illustrates the last stage.

In these examples the levels of iodine were measured by:
elemental analysis
argentometry
UV spectorscopy Furthermore, most of the products were characterized by acid-base titration in different solvents (water/wafer-acetone/DMSO).

All of the molecular masses were measured by steric exclusion chromatrography under high pressure, also designated as chromatography by gel permeation (GPC) in comparison with the starting dextrans. The masses thus determined are designated $M_{GPC}$ in what follows.

EXAMPLE 1

20 g of dextran (Dextran T40) from Pharmacia Fine Chemicals, indicated mean molecular mass in weight $Mw = 40,000$, $M_{GPC} = 27,000$) are dissolved in 165 ml of an aqueous solution of 6M sodium hydroxide at 0° C. The solution is stirred at this temperature for 20 minutes.

41 g of monochloroacetic acid are added to the reaction medium. The temperature is then brought to 60° C. and the solution is maintained for 20 minutes at this temperature with stirring. Ihe mixture is then cooled, then neutralized to pH 7.00 by the addition of concentrated HCl. The product is then precipitated with 1 liter of methanol, filtered off, washed and dried at 50° C. in a vacuum.

24 g of carboxymethyldextran sodium salt are obtained with a degree of substitution of 50% (determined by acid-base titration).

This same operation is repeated a second time: 26 g of carboxymethyldextran sodium salt are obtained with a degree of substitution of 80%.

The molecular mass of the polymer obtained, determined by the steric exclusion chromatography, is 47,000.

2 g of carboxymethyldextran with 3.50 meq/g of —COONa functions (80% substitution) are dissolved in 10 ml of water and the pH of the medium is brought to 2.50 by the addition of concentrated HCl. Furthermore, 2.6 g of N-ethoxycarbonyl-2-ethoxy-1,2-dihydroquinoline(EEDQ) are dissolved in 21 ml ethanol and added progressively to the reaction medium with homogeneous stirring. After 30 minutes, 4.6 g of iodinated amine of formula $$\text{HO(CH}_2)_2\text{—NH—CO} \quad \text{(VII)} \quad \text{NH—CO—CH}_2\text{—NH}_2$$

(2,4,6-triiodo-3-N-hydroxyethylcarbamoyl-5-aminoacetamido benzoic acid) dissolved in 3.5 ml of 2M sodium hydroxide are added to the reaction medium, the pH being fixed at 8.50.

The reaction is left at room temperature for 4 hours with stirring. Then the reaction medium is evaporated in a vacuum in order to remove the ethanol before being precipitated with 200 ml of methanol. The product is dried in a vacuum at 50° C.

The level of iodine in the polymer was estimated at 6.2%

A second fixation is carried out with the same amounts of reagent to result in a level of iodine of 16%.

A third with 1 eq of EEDQ and 0.9 eq of amine relative to the starting carboxymethyldextran makes it possible to bring the level of iodine to 24% After having been dried in a vacuum, the polymer is redissolved in water, ultrafiltered and lyophilized.

1.5 g of iodinated carboxymethyldextran in the form of a sodium salt are obtained with a molecular mass of 48,000 (determined by GPC). The polymer obtained exhibits grafting groups of formula

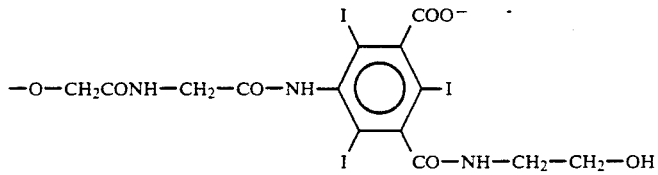

EXAMPLE 2

1.5 g of carboxymethyldextran (obtained previously in example 1) with 3.50 meq/g of —COOH functions in the acid form are dissolved dissolved in 10 ml of DMAC are added to the previous solution.

When the mixture is homogeneous, 3.6 g of iodinated amine of formula VII and 0.55 ml of triethylamine dissolved in 10 ml of water are added progressively. The solution is left at room temperature for 24 hours with stirring, then filtered in order to remove the precipitated amine and dicyclohexyl urea.

The filtrate is evaporated to dryness in a vacuum, taken up in water then ultrafiltered and lyophilized (the triethylamine salt being displaced by sodium hydroxide).

1.2 g of polymer, containing 8% of iodine with a molecular mass of 48,000 (determined by GPC) are obtained.

EXAMPLE 3

2 g of carboxymethyldextran (obtained in example 1) with 3.50 meq/g of —COONa functions dissolved in 5 ml of water and 1.5 g of iodinated amine of formula VII dissolved in 20 ml of 1N sodium hydroxide are mixed. The pH of the medium is brought to 3.00 by addition of HCl.

After 10 minutes, 1.6 g of 1-ethyl-3(3-dimethylaminopropyl)carbodiimide chloride are added. The pH is maintained constant between 4.5 and 5.0 for the first hour of reaction The solution is left at room temperature for 24 hours with stirring, then it is filtered. The filtrate is ultrafiltered and lyophilized.

1.9 g of polymer containing 15% of iodine, with a molecular mass of 54,000 (determined by GPC), are obtained.

EXAMPLE 4

The operating procedure is identical with example 3 but the amine used is the following

[Chemical structure diagram showing two iodinated benzene rings with substituents: first ring has COOH, I, I, I, OHCH$_2$CH$_2$NHCO, and NHCOCH$_2$NHCO; second ring has NHCOCH$_2$NH, I, I, I, and CONHCH$_3$]

(2.9 g are placed in reaction).

2.3 g of iodinated polymer containing 24.6% of iodine, with a molecular mass of 62,000 (determined by GPC), are obtained.

EXAMPLE 5

A carboxymethyldextran is prepared as in example 1 but by using as starting polymer Dextran T18 (Pharmacia Fine Chemicals, Mw=18,000, $M_{GPC}$=14,000).

The carboxymethyldextran is obtained with a degree of substitution of 70% and with a molecular mass of 29,000 (determined by GPC).

2 g of carboxymethyldextran with 3.20 meq/g of —COONa functions are dissolved in 10 ml of water and the pH of the medium is brought to 2.50 by addition of concentrated HCl. Furthermore, 2.4 g of N-ethoxycarbonyl-2-ethoxy-1,2-dihydroquinoline are dissolved in ml of ethanol and added progressively to the reaction medium with homogeneous stirring.

After 30 minutes, 5.9 g of iodinated amine of formula VII dissolved in 4.5 ml of 2M sodium hydroxide are added to the reaction medium, the pH being fixed at 8.50. The operating procedure is then identical with example 1.

The level of iodine in the polymer was estimated at 6.2%.

A second fixation (1.4 eq of EEDQ and 1.1 eq of amine relative to the carboxymethyldextran) makes it possible to obtain a level of iodine of 16%, a third fixation (1.3 eq of EEDQ and 1.0 eq of amine relative to the CMD) leads to a level of iodine of 24% in the polymer.

After having been dried in a vacuum, the polymer is redissolved in water, ultrafiltered and lyophilized.

1.9 g of iodinated carboxymethyldextran in the form of the sodium salt are obtained, with a molecular mass of 32,000 (determined by GPC).

EXAMPLE 6

A carboxymethyl dextran is prepared as in example 1 but Dextran T10 is used (Pharmacia Fine Chemicals, Mw=10,00 $M_{GPC}$=7,400).

The carboxymethyldextran is obtained with a degree of itution of 75% (3.5 meq/g) and with a molecular mass of 15,000 (determined by GPC) whereas that of the starting dextran is 7,400.

2 g of carboxymethyldextran with 3.35 meq/g of —COONa functions are dissolved in 10 ml of water and the pH of the medium is brought to 2.50 by addition of concentrated HCl. Furthermore, 2.5 g of N-ethoxycarbonyl-2-ethoxy-1,2-dihydroquinolien are dissolved in 20 ml of ethanol and added progressively to the reaction medium with homogeneous stirring.

After 30 minutes, 4.6 g of iodinated amine of formula VII dissolved in 3.5 ml of 2M sodium hydroxide are added to the reaction medium, the pH being fixed at 8.50.

The operating procedure is then identical with example 1.

The level of iodine in the polymer is estimated at 13%.

A second fixation (1.4 eq of EEDQ and 0.9 eq of amine relative to the carboxymethyldextran) makes it possible to obtain a level of iodine of 22%; a third fixation (1.0 eq of EEDQ and 1.0 eq of amine relative to the carboxymethyldextran) leads to a level of iodine of 26% in the polymer.

After having been dried in a vacuum, the polymer is redissolved in water, ultrafiltered and lyophilized.

1.8 g of iodinated carboxymethyldextran in the form of the sodium salt are obtained, with a molecular mass of 15,000 (determined by GPC).

EXAMPLE 7

0.25 g of carboxymethyldextran (obtained in example 1) with 3.50 meq/g of —COOH functions placed in the acid form are dissolved in 10 ml of dimethylformamide, then are added 3 ml of hexamethyldisilazane. The reaction medium is brought to 100° C. for 16 hours, then the latter is evaporated and taken up twice in DMF.

1.4 g of iodinated amine of formula VII are then added, the heating is brought to 50° C. for 6 hours. After cooling, the reaction is diluted with 100 ml of water. After 1 hour, the latter is concentrated then precipitated with methanol.

After having been dried in a vacuum, the polymer is redissolved in water, ultrafiltered and lyophilized.

0.2 g of iodinated carboxymethyldextran in the form of the sodium salt is obtained with a level of iodine of 19.8% and a molecular mass of 48,000 (determined by GPC).

EXAMPLE 8

2 g of carboxymethyldextran with 3.20 meq/g of —COONa functions (obtained from dextran of Mw 40,000) are dissolved in 10 ml of water, the pH of the medium is brought to 2.50 by addition of concentrated HCl. Furthermore. 2 equivalents of N-ethoxycarbonyl-2-ethoxy-1,2-dihydroquinoline and 1.5 eq of iodinated amine of formula VII are added according to the operating procedure described in example 1.

A second fixation is carried out with 1.5 eq of EEDQ and 1.5 eq of amine relative to the starting carboxymethyldextran 1.5 g of iodinated polymer containing 35% of iodine, with a molecular mass of 50,000, are obtained.

EXAMPLE 9

3 g of dextran (Mw=40,000, $M_{GPC}$=27,000) are dissolved in 30 ml of DMSO, 7.2 g of succinic anhydride in 35 ml of DMSO are added to the preceding solution as well as 1.8 g of 4-dimethylaminopyridine in the solid form. The solution is stirred for 4 hours at 45° C. The reaction medium is precipitated with methanol. After drying, it is redissolved in water, then ultrafiltered and lyophilized. 3 g of polymer are obtained with a level of substitution of 131%.

1 g of the polymer previously obtained with 4.87 meq/g of acidic functions is dissolved in 20 ml of DMSO with 1.6 g of carbonyldiimidazole.

The solution is stirred at room temperature for 30 minutes. Then 6 g of iodinated amine of formula VII dissolved in 4.5 ml of 2M sodium hydroxide are added; the stirring is maintained for 24 hours. The reaction medium is precipitated with methanol. After drying, the product is redissolved in water, ultrafiltered and lyophilized.

The polymer obtained possesses a level of iodine of 20%.

The polymer obtained exhibits grafting groups of formula

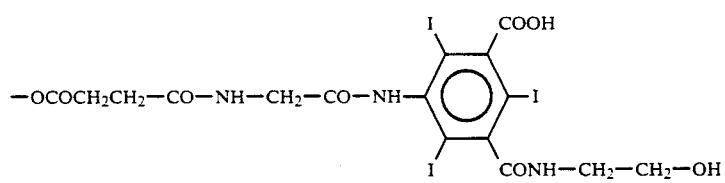

After 30 minutes, 1.2 g of ethanolamine (0.020 mole) are added to the reaction medium.

The reaction is left at room temperature for 24 hours with stirring. Then, the reaction medium is evaporated in a vacuum in order to remove the ethanol before being precipitated with 500 ml of methanol.

The product is dried in a vacuum at 50° C.

A second fixation of ethanolamine is carried out under the same conditions with the same amounts of reagents.

After having been dried in a vacuum, the polymer is redissolved in water, ultrafiltered; the solution is evaporated. The product obtained is taken up in ether, then dried in a vacuum at 50° C.

7.5 g of ethanolamine-modified iodinated carboxymethyldextran are obtained with

Mw=47,500
Mn=25,300
Polydispersion index=1.9

The polymer obtained exhibits

54% of grafting groups of formula —OCH$_2$CONHCH$_2$CH$_2$OH

30% of grafting groups of formula

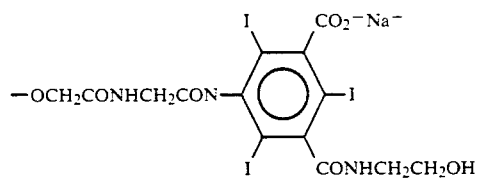

(% iodine = 26.6)

16% of unmodified carboxymethyl groups

| solubility % m/v | 33.7, i.e. 8.96% iodine |
|---|---|
| Osmolarity mOsm/Kg (20° C.) | 440 (cryoscopy) 875 (tonometry) |
| Viscosity mPa/s (37° C.) | 26 |

EXAMPLE 11

It was carried out as in example 10, but by using methylamine in the place of ethanolamine.

The iodinated polymer obtained has the following properties.

Mw=23,000
Mn=11,000
Polydispersion index: 2.1
Iodine concentration: 24.1%

EXAMPLE 12

It was carried out as in example 10, but by using 2,3-dihydroxypropylamine in the place of ethanolamine.

The iodinated polymer has the following properties:

EXAMPLE 10

10 g of iodinated carboxymethyldextran prepared as described in Example 1 (having a level of iodine of 25.5%, Mw=65,400, Mn=33,000; polydispersion index=2.0) are dissolved in 30 ml of water. The pH of the medium is brought to 3.50 by addition of concentrated HCl. Furthermore, 5.2 g (0.019 mole) of N-ethoxycarbonyl-2-ethoxy-1,2-dihydroquinoline are dissolved in 30 ml of ethanol and added progressively to the reaction medium with homogeneous stirring.

Mw=21,500
Mn=12,000
Polydispersion index: 1.8
Iodine concentration: 20%

Comparative results relating to the toxicity of the polymers before reaction and after reaction with an aliphatic amine will be given below.

| Polymer type | Example 1 before reaction | Example 10 after reaction |
|---|---|---|
| LD 50, IV mice (ml/Kg) | 12.9 | >50 |
| 2 ml/min (mEq glucose residue/Kg) | 9 | >39.1 |

These results demonstrate a toxicity more than 3 times lower for the polymer of example 10 obtained after reaction of an iodinated polymer with an aliphatic amine.

An object of the present invention is also contrast products which comprise at least one iodinated polymer such as defined above.

These contrast products can be used in man and animals for radiological purposes.

The preferred pharmaceutical form of the contrast products according to the invention is constituted by aqueous solutions of the polymers.

An example of a contrast product according to the present invention will be given below

| Contrast product | |
|---|---|
| Polymer of example 10 | 20 g |
| Water for injectable preparation Q.S.P. | 100 ml |

In a general manner, the contrast products according to the invention can be administered by all of the routes classically used for contrast products and, in particular, by the parenteral route (intravenous, intra-arterial, intra- or peri-lymphatic routes, subarachnoidal route (myelography)) and by the oral route.

The contrast products according to the present invention can be used in particular in angiography. They can usually be injected into man at doses of iodine of 30 to 500 mgI/kg.

We claim:

1. An iodinated polymer consisting essentially of a dextran backbone onto which are grafted groups of the formulae:

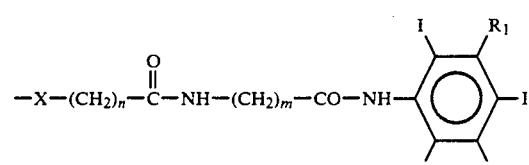 a)

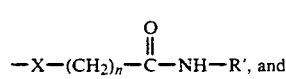 b)

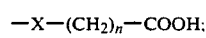 c)

wherein X is —NH—,

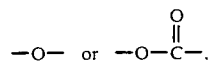

n is an integer from 0 to 4,
m is an integer from 1 to 5, $R_1$ is —COOH, —COOH made into a salt by a pharmaceutically acceptable base, or

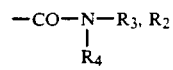

is

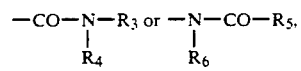

and R' is $C_{1-4}$ alkyl, $C_{1-4}$ hydroxyalkyl or poly($C_{1-4}$ hydroxyalkyl); in which $R_3$ and $R_5$ are each independently $C_{1-6}$ alkyl, $C_{1-6}$ hydroxyalkyl, poly($C_{1-6}$ hydroxyalkyl), $C_{1-6}$ alkoxy $C_{1-6}$ alkyl or $C_{1-6}$ alkoxy $C_{1-6}$ hydroxyalkyl, $R_4$ and $R_6$ are each independently H, or one of the values given for $R_3$ and $R_5$, and in which $R_3$ may also be

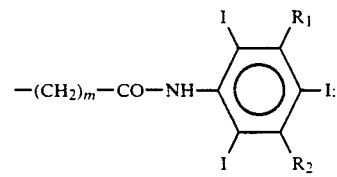

and wherein less than 20% of said grafted groups a), b) and c) are said groups c).

2. The polymer according to claim 1, wherein X is —O— and n is 1.

3. A method of making the polymer according to claim 1, comprising:

reacting a dextran with a grafting reagent having a chemical structure that converts the hydroxy groups of the dextran into grafting groups of the formula

 (IV)

reacting said grafting groups on said dextran with an amine of the formula

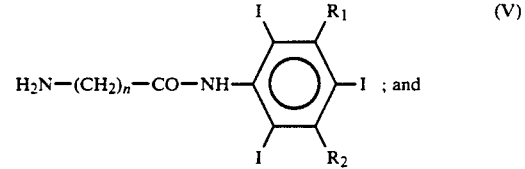 (V)

reacting the thus-obtained iodinated polymer with an amine of the formula

 (VI);

wherein Z is an activation group capable of reacting with the primary amino group of the amines (V) and (VI).

4. A contrast agent for radiography, consisting essentially of an aqueous solution of the polymer according to claim 1.

* * * * *

UNITED STATES PATENT AND TRADEMARK OFFICE
CERTIFICATE OF CORRECTION

PATENT NO. : 5,126,440
DATED : June 30, 1992
INVENTOR(S) : Dominique PARIS et al.

It is certified that error appears in the above—identified patent and that said Letters Patent is hereby corrected as shown below:

On the title page, under Item [22], change the filing date of the corresponding PCT application from "August 10, 1989" to --August 3, 1989--.

Signed and Sealed this

Nineteenth Day of October, 1993

Attest:

BRUCE LEHMAN

Attesting Officer      Commissioner of Patents and Trademarks